United States Patent [19]

Frigg

[11] Patent Number: 5,035,697
[45] Date of Patent: Jul. 30, 1991

[54] ORTHOPEDIC MEDULLARY NAIL

[75] Inventor: Robert Frigg, Davos, Switzerland

[73] Assignee: Synthes (U.S.A.), Paoli, Pa.

[21] Appl. No.: 547,238

[22] Filed: Jul. 3, 1990

[30] Foreign Application Priority Data

Mar. 20, 1990 [CH] Switzerland ............... 914/90

[51] Int. Cl.⁵ .................................. A61B 17/58
[52] U.S. Cl. ........................... 606/67; 606/60;
606/62; 606/72; 606/86; 606/74
[58] Field of Search ............ 606/60, 62, 68, 67,
606/86, 95, 96, 72, 74, 87

[56] References Cited

U.S. PATENT DOCUMENTS

| | | | |
|---|---|---|---|
| 4,589,883 | 5/1986 | Kenna | 606/62 X |
| 4,630,601 | 12/1986 | Harder et al. | 606/62 |
| 4,667,663 | 5/1987 | Miyata | 606/62 |
| 4,678,471 | 7/1987 | Noble et al. | 606/62 X |
| 4,846,162 | 7/1989 | Moehring | 606/67 |
| 4,898,186 | 2/1990 | Ikada et al. | 606/62 |

FOREIGN PATENT DOCUMENTS

| | | | |
|---|---|---|---|
| 0987983 | 4/1976 | Canada | 606/62 |
| 1031128 | 6/1953 | France | 606/62 |

Primary Examiner—Robert A. Hafer
Assistant Examiner—Brian E. Hanlon
Attorney, Agent, or Firm—Davis, Hoxie, Faithfull & Hapgood

[57] ABSTRACT

A tibia medullary pin for the treatment of lower-leg fractures of all kinds has an anterior half (1), a posterior half (2), a proximal end segment (3), and a distal end segment (4), with the longitudinal axes (5;6) of the two end segments (3;4) forming in the antero-posterior plane an angle of 5°–13° with each other. The proximal end segment (3) has a cross-section area (7) that is trigonal in both the anterior (1) and the posterior (2) halves, and overall is approximately rhombic, while the distal end segment (4) has a cross-section area (8) that is approximately trigonal in the anterior half (1) and is approximately semi-spherical in the posterior half (2).

14 Claims, 2 Drawing Sheets

ORTHOPEDIC MEDULLARY NAIL

FIELD OF THE INVENTION

The invention relates to an orthopedic medullary nail and in particular a medullary nail for the tibia.

BACKGROUND OF THE INVENTION

Medullary nailing is frequently used for the treatment of lower leg fractures. The function of the medullary nail amounts to an internal splinting of the long bone. Depending on the method, a conventional medullary nail can consist of a tube or a number of metal rods, so-called cluster nailing. When a tubular nail is used, as is described for example, in EP-A1 0 332 857, the medullary area of the long bone must be prepared by milling. By means of this milling procedure, a close fit is achieved between the nail and the interior wall of the bone. This method provides optimum splinting of the bone. However, a pre-condition for the use of this method is that the bone fracture be able to accept axial and torsional forces.

The same restriction holds true in cluster nailing, in which the non-milled medullary area is filled with long metal rods. This type of splinting is heavily dependent on the skill of the individual surgeon, since it is not easy to fill the entire medullary space with metal rods.

If there is no bony support of the bone fracture itself (as because of fragmentation or bone defects), medullary bolting must be performed. For this type of medullary nailing, no fitting of the medullary area is necessary. Nevertheless, except in lengthy fragmented areas, the medullary area must usually be milled, since medullary nails that can be bolted have a certain minimum diameter and are somewhat stiffer.

Tubular medullary nails, for example, nails according to EP-A1 0 332 857, are shaped according to the milled medullary area. Tubular nails that cannot be bolted usually have a cloverleaf cross-section and a partial or complete longitudinal slot. The advantage of this is that the nail can be braced radially in the milled medullary area, with consequent increased stability of the fracture to impinging rotational forces. However, such bracing requires a dimensionally precise milling of the medullary area, to prevent the nail from becoming stuck when it is inserted. In bolting, radial prestressing is not done, since the fracture is secured by the transverse screws. The cross-section of such medullary nails is therefore approximately circular, so that it can be easily inserted into the milled medulla.

An attempt to hammer a tubular medullary nail into a non-milled medullary area requires a major expenditure of force, since the tibia cross-section does not correspond to the cross-section of the medullary nail. In this case a breaking of the tibia shaft often occurs, along with seizure of the nail.

To avoid the aforementioned problems, a thinner medullary nail can be selected. However, this is not always possible, since the mechanical strength of tubular pins is, by their very nature, limited. This limit can easily be reached, since this type of medullary pin possesses no rotation resistance; that is, in addition to the axially operative forces, rotational forces must also be borne fully by the transverse screws or pins.

SUMMARY OF THE INVENTION

In accordance with the invention there is provided an intramedullary nail for treating lower leg fractures of all kinds having its shape optimally adapted to the anatomy of the tibial medulla. The pin has high rotational stability in the proximal spongy portion of the tibia, guaranteeing optimum adaption to the geometry of the cavity in the distal, cortical portion.

A nail according to the invention has an anterior half, a posterior half, a proximal end segment having a longitudinal axis and a distal end segment having a longitudinal axis, the axes of the end segments forming an angle in the anterior-posterior plane of from about 5° to about 13°, the posterior and anterior halves of the proximal end segment being generally trigonal in cross-section, the overall cross-section of the proximal end segment being generally rhombic, the anterior half of the distal end segment being generally trigonal in cross section and the posterior half generally semicircular in cross-section. Both segments of the nail are solid, not tubular.

BRIEF DESCRIPTION OF THE DRAWINGS

The invention will be further described with reference to the accompanying drawings in which:

Referring to FIG. 1, a tibia medullary nail according to the invention is made as a solid piece of a metallic substance having a composition customary for such implants. It has an anterior side 1 and a posterior side 2, and comprises a proximal end segment 3 and a distal end segment 4, angled toward each other. Longitudinal axes 5 and 6 of the two end segments 3 and 4 form an angle A of from 5° to 13°, preferably 7° to 11° and most preferably 8° to 10°, usually about 9°, in the sagittal plane, which corresponds to the plane of the FIG. 1.

Figure 1:
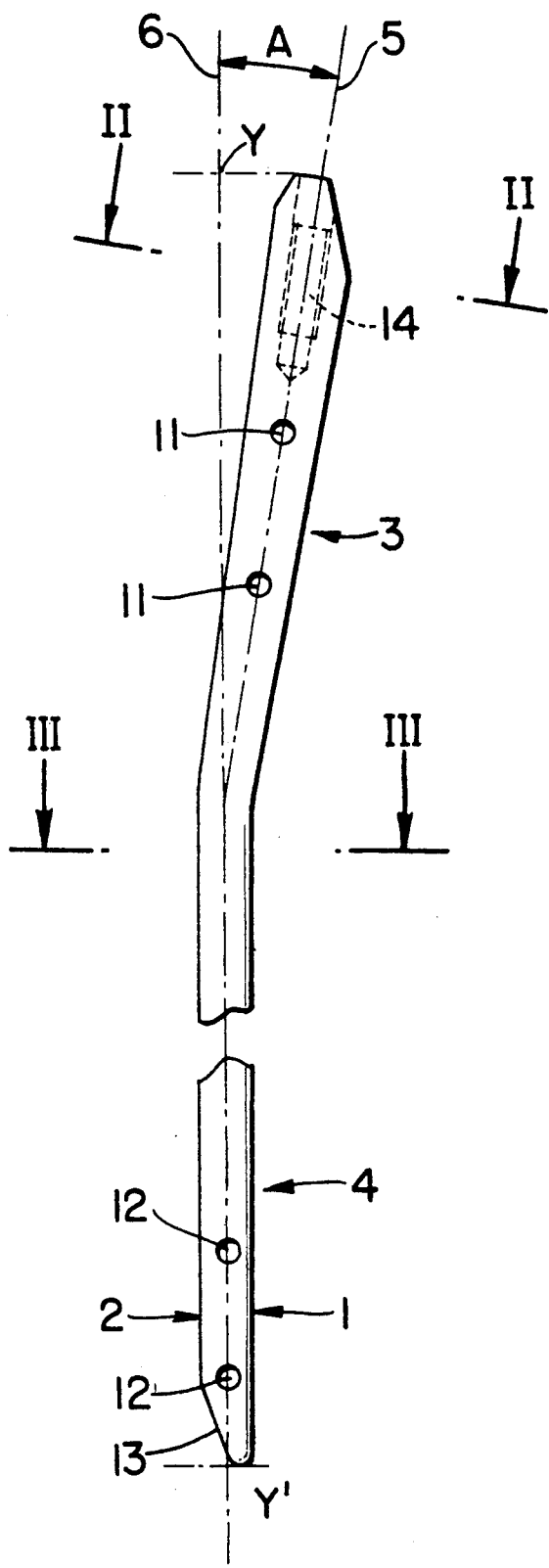
FIG. 1 is a side elevational view of a tibia medullary pin according to the invention.

The proximal end segment 3 of the medullary pin has a transverse shape, (FIG. 2) which is trigonal, both in the anterior half 1 and in the posterior half 2, so that there is overall a rhombic, preferably a square, profile 7.

The distal end segment 4 has a cross-section 8, (FIG. 3) which is similarly trigonal in the anterior half 1. The posterior half 2 is semi-spherical.

The proximal end segment 3 has two bolt holes 11, running mediolaterally, for locking screws (not shown).

The proximal end segment 3 has at its proximal end a threaded socket 14, to receive an appropriate instrument for the inserting and removing of the nail.

The distal end segment 4 has at its tip a step 13 oriented toward the rear, which facilitates insertion of the nail into the medullary space through practically frictionless sliding along the dorsal inner cortical.

Figure 2:
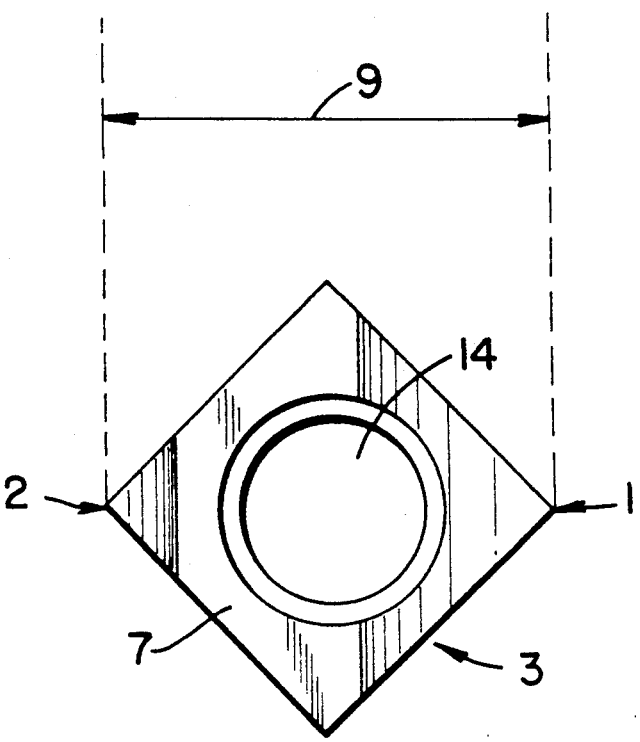
FIG. 2 is a top view of the proximal end segment from a point on the axis 5 of FIG. 1.

Referring to FIG. 2 the maximum diameter 9 of the proximal end segment 3, measured in antero-posterior direction, at point II—II is from 12 to about 13 mm and narrows continuously from proximal to distal to from about 8 to about 9 mm.

Figure 3:
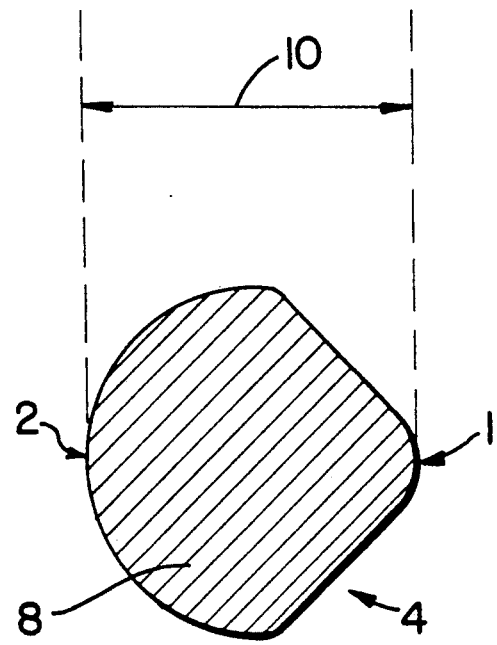
FIG. 3 is a cross-section along line III—III of FIG. 1.

As shown in FIG. 3 the maximum diameter 10 of distal end segment 4, measured in antero-posterior direction, remains essentially the same from proximal to distal.

The absolute dimensions of the pin can be varied, depending on anatomical requirements. However, it has proved advantageous to have the length of the proximal end segment from about 30 to about 35%, preferably from about 33 to about 34% of the overall length of the nail, measured along the extended axis 6 of the distal segment, from Y to Y' in FIG. 1.

A tibia medullary nail according to the invention, is bent in the antero-posterior plane, and has different cross-sections at the proximal and distal end segments in order to meet the differing requirements in these two areas. The generally rhombic cross-section of the proximal end segment improves rotational stability in this mostly spongy segment of the tibia. The anterior side of the distal end segment has the same design as the proximal end segment; in contrast, the posterior side is semispherical, so that it can be better adapted to the shape of the bone cavity in this area.

The posterior side of the medullary pin, which in the distal area is spherical in shape, facilitates easy insertion of the implant, which, thanks to this shape, can easily slide along the posterior interior wall of the tibia. The anterior side of the medullary pin cross-section, which in the distal area is trigonal, corresponds to the side of the unmilled tibia medullary cross-section. In addition to rotation security, the advantage of this cross-section is that a pin having a cross-section larger, by comparison, than that of a pin with circular cross-section can be used. The danger of implant breakage is therefore less.

Fundamentally, the solid pin cross-section has two advantages. After implantation there is no cavity in the medullary channel which might lead to problems in treating an open fracture. Moreover, the pin cross-section is less weakened in the area of the bolt holes. When tubular pins are used, the cavity created in the medullary area can lead to problems in the treatment of open fractures, since the body cannot assimilate foreign bodies that may be inserted into it, something that leads to the risk of infection.

The medullary nail with its cross section adapted according to the invention, thanks to its anatomical shape, can be slid into the medullary area without a major effort. The advantage of this is that there is no need to fear additional injuries to the tibia in relation to soft tissue damage, blood supply, and dispersal of fragments.

What is claimed is:

1. A medullary nail for the tibia having an anterior half, a posterior half, a proximal end segment having a longitudinal axis, and a distal end segment having a longitudinal axis, the axes of the proximal and distal end segments meeting at an angle in the anterior-posterior plane of from about 5° to about 13°, the posterior and anterior halves of the proximal end segment being generally trigonal in cross section and the cross section of the proximal end segment, as a whole, being generally rhombic, the anterior half of the distal end segment being generally trigonal in cross section and the posterior half being generally semi-circular in cross section.

2. The tibia medullary nail claimed in claim 1, wherein the trigonal anterior cross-section of the distal end segment is rounded off toward the anterior.

3. The tibia medullary nail claimed in claim 1, wherein the length of the proximal end segment is between about 30 and about 35%, of the entire length of the medullary nail.

4. The tibia medullary nail claimed in claim 3, wherein the proximal end segment is between about 33% and about 34% of the length of the nail.

5. The tibia medullary nail claimed in claim 1, wherein the thickness of proximal end segment, measured in antero-posterior direction, continuously diminishes from proximal to distal.

6. The tibia medullary nail claimed in claim 1 where the thickness of the proximal end segment in the antero-posterior direction decreases from about 12 to about 13 mm at its proximal end to from about 8 to about 9 mm at its distal end.

7. The tibia medullary nail according to claim 1, wherein the maximum diameter of the distal end segment, measured in antero-posterior direction, remains essentially the same from proximal to distal.

8. The tibia medullary nail claimed in claim 1 wherein both segments are solid.

9. The tibia medullary nail claimed in claim 1, wherein the proximal end segment has at least one bolt hole.

10. The tibia medullary nail claimed in claim 1, wherein the distal end segment has at least one bolt hole.

11. The tibia medullary nail claimed in claims 6 or 7, wherein the bolt holes run in the medio-lateral direction.

12. The tibia medullary nail claimed in claim 1, wherein the distal end segment has at its tip a step posteriorly oriented.

13. The tibia medullary nail claimed in claim 1, wherein the longitudinal axes of the two end segments form in the antero-posterior plane an angle of from about 7° to 11°.

14. The tibia medullary nail claimed in claim 13 wherein the longitudinal axes of the two end segments form in the antero-posterior plane an angle of from about 8° to about 10°.

* * * * *